US006225525B1

(12) United States Patent
Leung et al.

(10) Patent No.: US 6,225,525 B1
(45) Date of Patent: May 1, 2001

(54) ATP-BINDING CASSETTE TRANSPORTER (ABC1) MODIFIED TRANSGENIC MICE

(75) Inventors: Wai-Ping Leung; Trudy Christiansen-Weber; Joseph R. Voland, all of San Diego, CA (US); Per A. Peterson, Bedminster, NJ (US)

(73) Assignee: Ortho-McNeil Pharmaceutical, Inc., Raritan, NJ (US)

(*) Notice: Subject to any disclaimer, the term of this patent is extended or adjusted under 35 U.S.C. 154(b) by 0 days.

(21) Appl. No.: 09/417,619

(22) Filed: Oct. 13, 1999

(51) Int. Cl.[7] ........................ A01K 67/027; C12N 15/00; C12N 15/63; C12N 15/90

(52) U.S. Cl. .................................. 800/18; 800/9; 800/21; 800/25; 435/455; 435/461; 435/463

(58) Field of Search .............................. 800/8, 9, 13, 14, 800/18, 21, 25; 435/455, 461, 463

(56) References Cited

PUBLICATIONS

Weng, J. et al. Insights into the function of Rim protein in photoreceptors and etiology of Stargardt's disease from the phenotype in abcr knockout mice. Cell 98:13–23, 1999.*

Young, S.G. & Fielding, C.J. The ABCs of cholesterol efflux. Nat. Genetics 22:316–318, 1999.*

Allikmets, Rando; Singh, Nanda; Sun, Hui; Shroyer, Noah F.; Hutchinson, Amy; Chidambaram, Abirami; Gerrard, Bernard; Baird, Lisa; Stauffer, Dora; Peiffer, Andy; Rattner, Amir; Smallwood, Philip; Li, Yixin; Anderson, Kent L.; Lewis, Richard Alan; Nathans, Jeremy; Leppert, Mark; Dean, Michael; Lupski, James R. A photoreceptor cell–specific ATP–binding transporter gene (ABCR) is mutated in recessive Stargardt macular dystrophy. Nature genetics, vol. 15, Mar. 1997, pp. 236–246.

Assmann, Gerd; von Eckardstein, Arnold; Brewer, H. Bryan Jr. Familial High Density Lipoprotein Deficiency: Tangier Disease. The Metabolic and Molecular Bases of Inherited Disease, Seventh Edition, vol. II, Chapter 64. pp. 2053–2072.

Bodzioch, Marek; Orso, Evelyn; Klucken, Jochen; Langmann, Thomas; Bottcher, Alfred; Diederich, Wendy; Drobnik, Wolfgang; Barlage, Stefan; Buchler, Christa; Porsch–Ozcurumez, Mustafa; Kaminski, Wolfgang E.; Hahmann, Harry W.; Oette, Kurt; Rothe, Gregor; Aslanidis, Charalampos; Lackner, Karl J.; Schmitz, Gerd. The gene encoding ATP–binding cassette transporter 1 is mutated in Tangier disesase. Nature Genetics, vol. 22, Aug. 1999, pp. 347–351.

Brooks–Wilson, Angela; Marcil, Michel; Clee, Susanne M,; Zhang, Lin–Hua; Roomp, Kirsten; van Dam, Marjel; Yu, Lu; Brewer, Carl; Collins, Jennifer A.; Molhuizen, Henri O.F.; Loubser, Odell; Ouelette, B.F. Francis; Fichter, Keith; Ashbourne–Excoffon, Katherine J.D.; Sensen, Christoph W.; Scherer, Stephen; Mott, Stephanie; Denis, Maxime; Martindale, Duane; Frohlich, Jiri; Morgan, Kenneth; Koop, Ben; Pimstone, Simon; Kastelein, John J.P.; Genest Jr., Jacques; Hayden, Michael R. Mutations in ABC1 in Tangier disease and familial high–density lipoprotein defiency. Nature genetics, vol. 22, Aug. 1999, pp. 336–345.

Connors, Timothy D.; Van Raay, Terence J.; Petry, Linda R.; Klinger, Katherine W.; Landes, Gregory M.; Burn, Timothy C. The Cloning of a Human ABC Gene (ABC3) Mapping to Chromosome 16p13.3. Genomics 39, 231–234, 1997.

Gartner, Jutta; Moser, Hugo; Valle, David. Mutations in the 70K peroxisomal membrane protein gene in Zellweger Syndrome. Nature Genetics, vol. 1, Apr. 1992, pp. 16–23.

Gottesman, Michael M.; Pastan, Ira. Biochemistry of Multidrug Resistance Mediated by the Multidrug Transporter. Annu. Rev. Biochem., 62:385–427, 1993.

Higgins, Christopher F. ABC–transporters: From Microorganisms to Man. Annu. Rev. Cell Biol. 8:67–113 (1992).

Langmann, Thomas; Klucken, Jochen; Reil, Markus; Liebisch, Gerhard; Luciani, Marie–Francoise; Chimini, Giovanna; Kaminski, Wolfgang E.; Schmitz, Gerd. Molecular Cloning of the Human ATP–Binding Cassette Transporters 1(hABC1): Evidence for Sterol–Dependent Regulation in Macrophages. Biochemical and Biophysical Research Communications, 257, 29–33, 1999.

Luciani, Marie Franciose; Denizot, Francios; Savary, Stephane; Mattei, Marie Genevieve; Chimini, Giovanna. Cloning of Two Novel ABC Transporters Mapping on Human Chromosome 9. Genomics 21, 150–159 (1994).

Luciani, Marie Franciose; Chimini, Giovanna. The ATP binding cassetete transporter ABC1, is required for the engulfment of corpses generated by apoptotic cell death. The EMBO Journal, vol. 15, No. 2, pp. 226–235, 1996.

Mosser, Jean; Douar, Anne–Marie; Sarde, Claude–Olivier; Kioschis, Petra; Fell, Robert; Moser, Hugo; Poustka, Anne–Marie; Mandel, Jean–Louis; Aubourg, Patrick. Putative X–linked adrenoleukodystrophy gene shares unexpected homology with ABC transporters. Letters to Nature, vol. 361, Feb. 25, 1993, pp. 726–730.

Riordan, John R.; Rommens, Johanna M.; Kerem, Bat–Sheva; Alon, Noa; Rozmahel, Richard; Grzelczak, Zbyszko; Zielenski, Julian; Lok, Si; Plavsic, Natasa; Chou, Jia–Ling; Drumm, Mitchell L.; Iannuzzi, Michael C.; Collins, Francis S.; Tsui, Lap–Chee. Identification of the Cystic Fibrosis Gene: Cloning and Characterization of Complementary DNA. Science, vol. 245, pp. 1066–1073, 1989.

(List continued on next page.)

Primary Examiner—Karen M. Hauda
Assistant Examiner—Quang Nguyen
(74) Attorney, Agent, or Firm—John W. Wallen, III

(57) ABSTRACT

A transgenic mouse with alterations in an abc1 gene is prepared by introduction of an altered abc1 gene into a host animal. The resulting transgenic mice do not produce functional ABC1 protein molecules. Cells and cell lines derived from these animals also contain the altered abc1 gene.

6 Claims, 9 Drawing Sheets

OTHER PUBLICATIONS

Rust, Stephan; Rosier, Marie; Funke, Harald; Real, José; Amoura, Zahir; Piette, Jean–Charles; Deleuze, Jean–Francois; Brewer, H. Bryan; Duverger, Nicolas; Denefle, Patrice; Assmann, Gerd. Tangier disease is caused by mutations in the gene encoding ATP–binding cassette transporter 1. Nature Genetics, vol. 22, No. 22, Aug. 22, 1999, pp. 352–355.

Simmons, Donna M.; Arriza, Jeffrey L.; Swanson, L.W. A Complete Protocol for In Situ Hybridization of Messenger RNAs in Brain and Other Tissues With Radio–labeled Single–Stranded RNA Probes. The Journal of Histotechnology/ vol. 12, No. 3, Sep. 1989, pp. 169–181.

* cited by examiner

FIGURE 3 PANEL 1

ABC1 TRANSGENIC MOUSE

WILDTYPE MOUSE

FIGURE 3 PANEL 2

ABC1 TRANSGENIC MOUSE

WILDTYPE MOUSE

FIGURE 3 PANEL 3

5

FIGURE 3 PANEL 4

ABC1 TRANSGENIC MOUSE

WILDTYPE MOUSE

FIGURE 3 PANEL 5

ABC1 TRANSGENIC MOUSE

WILDTYPE MOUSE

FIGURE 4 PANEL 1

ABC1 TRANSGENIC MOUSE

5

WILDTYPE MOUSE

FIGURE 4 PANEL 2

ABC1 TRANSGENIC MOUSE

5

WILDTYPE MOUSE

SEQUENCE LISTING

<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:
      oligonucleotide 5' primer ABC3057

<400> SEQUENCE: 1
gagcacatct ggttctatgc                                           20

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence:
      oligonucleotide 5' primer Neo1455

<400> SEQUENCE: 2
gcttcctcgt gctttacggt at                                        22

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence:
      oligonucleotide 3' primer ABC210R

<400> SEQUENCE: 3
aagacacggt gctgctactg tt                                        22

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:
      oligonucleotide ABC547

<400> SEQUENCE: 4
cctacctgct gccttaaatc t                                         21

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:
      oligonucleotide ABC800R

<400> SEQUENCE: 5
atgctacagt tcctacaagc                                           20

ATP-BINDING CASSETTE TRANSPORTER (ABC1) MODIFIED TRANSGENIC MICE

FIELD OF THE INVENTION

The present invention relates to transgenic nonhuman animals wherein an abc1 gene is altered, producing an animal lacking functional ATP-binding cassette transporter (ABC1) protein.

BACKGROUND OF THE INVENTION

The ABC superfamily is comprised of myriad transmembrane proteins involved in the transport of vitamins, peptides, ions, sugars and amino acids (Higgins, C. F. ABC-transporters: from microorgansism to man. *Annu. Rev. Cell Biol.* 8, 67–113 (1992)). A subset of the superfamily contains four closely related proteins (ABC1, ABC2, ABC3 and ABCR) (Luciani, M. F., Denizot, F., Savar, S., Mattei, M. G. & Chimini, G. Cloning of two novel ABC transporters mapping on human chromosome 9. *Genomics* 21, 150–159 (1994). Connors, T. D. et al. The cloning of a human ABC gene (ABC3) mapping to chromosome 16p13.3. *Genomics* 39, 231–234 (1997). Allikmets, R. et al. A photoreceptor cell-specific ATP-binding transporter gene (ABCR) is mutated in recessive Stargardt macular dystrophy. *Nature Genet.* 15, 236–246 (1997)). The protein structure of this subfamily consists of two halves joined by a linker region, each with six transmembrane domains and an ATP-binding cassette site. Several diseases are the result of a dysfunctional ABC transporter—cystic fibrosis, Zellweger syndrome, adrenoleukodystrophy, multidrug resistance and Stargardt macular dystrophy—though the underlying molecular mechanism of the disease is seldom known (Allikmets, R. et al. A photoreceptor cell-specific ATP-binding transporter gene (ABCR) is mutated in recessive Stargardt macular dystrophy. *Nature Genet.* 15, 236–246 (1997). Riordan, J. R. et al. Identification of the cystic-fibrosis gene—cloning and characterization of complementary-DNA. *Science* 245, 1066–1072 (1989). Gartner, J., Moser, H. & Valle, D. Mutations in the 70k peroxisomal membrane-protein gene in Zellweger syndrome. *Nature Genet.* 1, 16–23 (1992). Mosser, J. et al. Putative X-linked adrenoleukodystrophy gene shares unexpected homology with ABC transporters. *Nature* 361, 726–730 (1993). Gottesman, M. M. & Patan, I. Biochemistry of multidrug resistance mediated by the multidrug transporter. *Annu. Rev. Biochem.* 62, 385–428).

The relationship between TD (Tangier disease), FHA (familial hypoalphalipoproteinemia) and mutation in the human ABC1 gene has recently been established by positional cloning of hABC1 from several different families bearing TD or FHA (Bodzioch, M. et al. The gene encoding ATP-binding cassette transporter 1 is mutated in Tangier disease. *Nature Genet.* 22, 347–351 (1999). Brooks-Wilson, A. et al. Mutations in ABC1 in Tangier disease and familial high-density lipoprotein deficiency. *Nature Genet.* 22, 336–345. Rust, S. et al. Tangier disease is caused by mutations in the gene encoding ATP-binding cassette transporter 1. *Nature Genet.* 22, 352–355 (1999)). In each case, point mutations, deletions or frameshifts creates a non-functional or truncated hABC1 protein. Individuals suffer from reduced or absent HDL-C and lower serum cholesterol and may exhibit discolored tonsils, enlarged spleen and lymph nodes, corneal clouding and neuropathy due to deposition of cholesteryl esters. In other cholesterol metabolic diseases such as Apo A-I deficiency, LCAT deficiency and Fish Eye disease, HDL-C is also reduced but serum cholesterol levels remain normal (Assmann, G., von Eckardstein, A. & Brewer, H. B. Jr Familial high density lipoprotein deficiency: Tangier disease. in *The Metabolic and Molecular Basis of Inherited Disease* (eds Scriver, C. R. et al.) 2053–2072 (McGraw-Hill, New York, 1995)). Low levels of HDL-C usually indicate a high-risk factor for coronary heart disease. Interestingly, the loss of HDL-C in TD patients does not generally cause predisposition to coronary heart disease.

Tangier disease is exceedingly rare, with only 40 reported families worldwide exhibiting the trait. As such, except for the absence of HDL-C, it is difficult to evaluate which symptoms may be directly attributed to a dysfunctional ABC1 transporter. The murine model of Tangier disease, which is described here, confirms the association of ABC1 with TD and exhibits other phenotypes which have not yet been described in humans. The model may further elucidate why the loss of HDL-C does not directly cause coronary heart disease in TD patients.

The human ATP-binding cassette transporter 1 (hABC1), a member of the ABC superfamily, has recently been cloned and analyzed. Frameshift mutations and single base-pair deletions resulting in truncation of hABC1 have been described and linked to familial HDL deficiency (familial hypoalphalipoproteinemia or FHA) and Tangier disease (TD). Both diseases are characterized by the lowering or lack of HDL-C. Low serum cholesterol, splenomegaly, enlarged lymph nodes and the deposition of cholesteryl esters in the reticuloendothelial system are also associated with TD.

SUMMARY OF THE INVENTION

To understand the functional role of ABC1 in different cell types, mice that do not express the functional ABC1 were generated by homologous recombination (HR) in embryonic stem (ES) cells. These mice provide a valuable animal model and tools to understand the function of ABC1 and to evaluate the therapeutic effects of drugs that modulate the function or the expression of ABC1 equivalents in human cells.

DETAILED DESCRIPTION OF THE INVENTION

Figure 1:
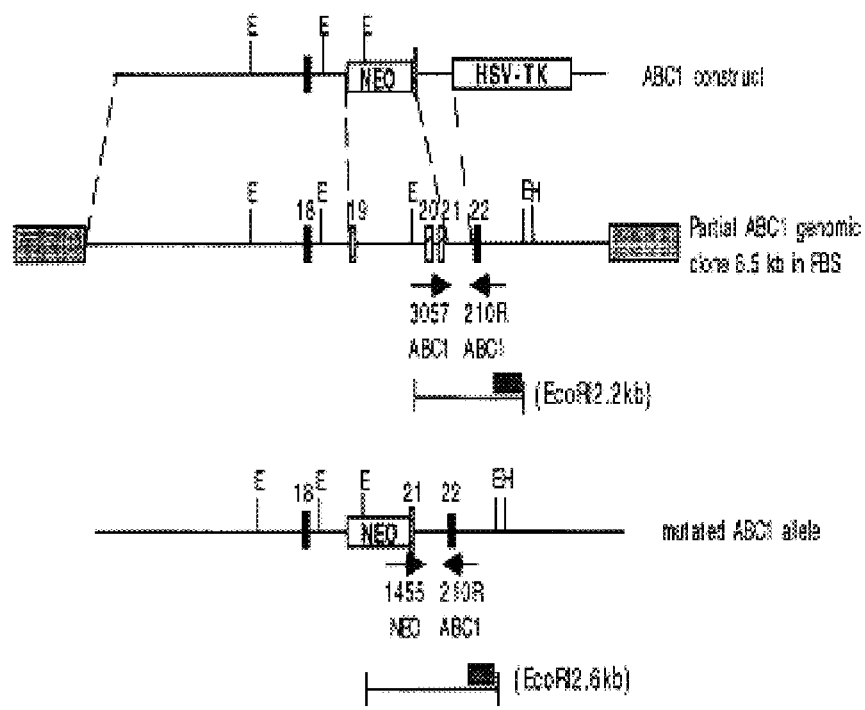
FIGS. 1A–C: Construction and verification of ABC1 knockout. A) Disruption of the abc1 gene. Genomic DNA fragment containing exons 18–22 of the abc1 gene is shown. Exons 19, 20 and part of 21 that encode most of the first ATP binding cassette of the ABC1 protein were replaced with a neomycin resistance gene. Arrows denote PCR primers used to verify genotype. Small gray bar denotes hybridization probe used in Southern blot analysis. E=EcoRI, H=HinDIII B) Agarose gel of PCR amplified bands: lane 1–2 homozygote, lane 3–4 heterozygote, lane 5–6 wild-type. B) Southern blot analysis of EcoRI digest of genomic DNA. Lane 1 wild-type, lane 2 and 3 heterozygote (mouse lines 55.2 and 64.7).
Figure 1:
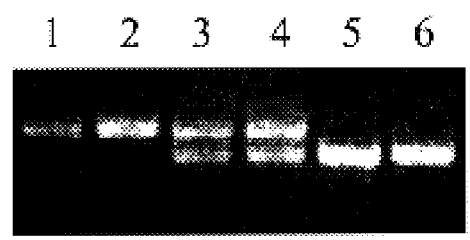
Figure 1:
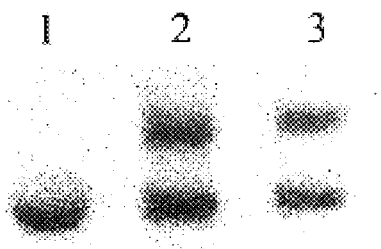

The ABC1 knockout mice were generated in the present invention by disruption of the abc1 gene by homologous recombination (HR). The process of generating the knockout mice can be divided into 4 basic stages:

1. cloning of abc1 gene and preparation of DNA construct for transfection of embryonic stem (ES) cells;
2. isolating ES cells in which the abc1 gene has been disrupted by HR;
3. generating chimeric mice from mouse embryos injected with the knockout ES cells; and
4. breeding chimeric mice to obtain knockout mice through germline transmission.

The present invention utilizes a cloned genomic DNA encoding the ABC1 protein and describes the cloning and characterization of the mouse abc1 gene. Transgenic animals are generated which have an altered abc1 gene. The alterations to the naturally occurring gene can be modifications, deletions and substitutions. Modifications and deletions render the naturally occurring gene nonfinctional, producing a "knockout" animal. Substitution of the naturally occurring gene for a gene from a second species results in an animal which produces the gene product of the second species. Substitution of the naturally occurring gene for a gene having a mutation results in an animal which produces the mutated gene product. These transgenic animals are critical for drug antagonist or agonist studies, the creation of animal models of human diseases, and for eventual treatment of disorders or diseases associated with ABC1-mediated responses. A transgenic animal carrying a "knockout" of ABC1 is useful for the establishment of a nonhuman model for diseases involving ABC1 equivalents in the human.

A transgenic mouse carrying the disrupted abc1 gene was generated by homologous recombination of a target DNA construct with the endogenous gene in the chromosome. The DNA construct was prepared from a genomic clone of ABC1 that was isolated from a genomic DNA library.

The term "animal" is used herein to include all vertebrate animals except humans. It also includes an individual animal in all stages of development, including embryonic and fetal stages. A "transgenic animal" is any animal containing one or more cells bearing genetic information altered or received, directly or indirectly, by deliberate genetic manipulation at a subcellular level, such as by targeted recombination or microinjection or infection with recombinant virus. The term "transgenic animal" is not intended to encompass classical cross-breeding or in vitro fertilization, but rather is meant to encompass animals in which one or more cells are altered by, or receive, a recombinant DNA molecule. This recombinant DNA molecule may be specifically targeted to a defined genetic locus, may be randomly integrated within a chromosome, or it may be extrachromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring in fact possess some or all of that alteration or genetic information, they are transgenic animals as well.

The alteration or genetic information may be foreign to the species of animal to which the recipient belongs, or foreign only to the particular individual recipient, or may be genetic information already possessed by the recipient. In the last case, the altered or introduced gene may be expressed differently than the native gene, or not expressed at all.

The altered abc1 gene generally should not fully encode the same ABC1 as native to the host animal, and its expression product should be altered to a minor or great degree, or absent altogether. However, it is conceivable that a more modestly modified abc1 gene will fall within the scope of the present invention.

The genes used for altering a target gene may be obtained by a wide variety of techniques that include, but are not limited to, isolation from genomic sources, preparation of cDNAs from isolated mRNA templates, direct synthesis, or a combination thereof.

A type of target cell for transgene introduction is the embryonal stem cell (ES). ES cells may be obtained from pre-implantation embryos cultured in vitro [M. J. Evans et al., Nature 292: 154–156 (1981); M. O. Bradley et al., Nature 309: 255–258 (1984); Gossler et al. Proc. Natl. Acad. Sci. USA 83: 9065–9069 (1986); Robertson et al., Nature 322, 445–448 (1986); S. A. Wood et al. Proc. Natl. Acad. Sci. USA 90: 4582–4584 (1993)]. Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal (R. Jaenisch, Science 240: 1468–1474 (1988)).

Since ABC1 is an independent component of a complex mechanism, the proteins, including that encoded by abc1 DNA, must be examined both individually and as a group if their contribution to the mechanisms are to be understood. One approach to the problem of determining the contributions of individual genes and their expression products is to use isolated genes to selectively inactivate the native wild-type gene in totipotent ES cells (such as those described herein) and then generate transgenic mice. The use of gene-targeted ES cells in the generation of gene-targeted transgenic mice was described in 1987 (Thomas et al., Cell 51:503–512, (1987)) and is reviewed elsewhere (Frohman et al., Cell 56:145–147 (1989); Capecchi, Trends in Genet. 5:70–76 (1989); Baribault et al, Mol. Biol. Med. 6:481–492, (1989); Wagner, EMBO J. 9: 3025–3032 (1990); Bradley et al., Bio/Technology 10: 534–539 (1992)).

Techniques are available to inactivate or alter any genetic region to any mutation desired by using targeted homologous recombination to insert specific changes into chromosomal genes. Homologous recombination was reported to be detected at frequencies between $10^{-6}$ and $10^{-3}$ (Lin et al., Proc. Natl. Acad. Sci. USA 82:1391–1395 (1985); Smithies et al., Nature 317: 230–234 (1985); Thomas et al., Cell 44:419–428, (1986); Song et al., Proc. Natl. Acad. Sci. USA 84:6820–6824 (1987)). Nonhomologous plasmid-chromosome interactions are more frequent, occurring at levels $10^5$-fold (Lin et al., Proc. Natl. Acad. Sci. USA 82:1391–1395 (1985)) to $10^2$-fold (Thomas et al., Cell 44:419–428 (1986); Song et al., Proc. Natl. Acad. Sci. USA 84:6820–6824 (1987)) greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening individual clones (Kim et al., Nucleic Acids Res. 16:8887–8903 (1988); Kim et al., Gene 103:227–233 (1991)). Alternatively, a positive genetic selection approach has been developed in which a marker gene is constructed which will only be active if homologous insertion occurs, allowing these recombinants to be selected directly (Sedivy et al., Proc. Natl. Acad. Sci. USA 86:227–231 (1989)). One of the most powerfiil approaches developed for selecting homologous recombinants is the positive-negative selection (PNS) method developed for genes (such as ABC1) for which no direct selection of the alteration exists (Mansour et al., Nature 336:348–352: (1988); Capecchi, Science 244:1288–1292, (1989); Capecchi, Trends in Genet. 5:70–76 (1989)). The PNS method is more efficient for targeting genes which are not expressed at high levels because the marker gene has its own promoter. Nonhomologous recombinants are selected against by using the Herpes Simplex virus thymidine kinase (HSV-TK) gene flanking the DNA construct. Cells with nonhomologous insertion of the construct express HSV thymidine kinase and therefore are sensitive to the herpes drugs such as ganciclovir (GANC) or FIAU (1-(2-deoxy 2-fluoro-B-D-arabinofluranosyl)-5-iodouracil). By this counter-selection, the number of homologous recombinants in the surviving transformants can be increased.

As used herein, a "targeted gene" or "knockout" is a DNA sequence introduced into the germline of a non-human animal by way of human intervention, including but not limited to, the methods described herein. The targeted genes of the invention include DNA sequences which are designed to specifically alter cognate endogenous genes.

All the above applications have to be verified in animal tests and eventually clinical trials. One approach to determine the functional role of the drug target is to study the defects resulting from the disrupted gene in a whole animal. The ABC1 knockout mice that have been generated and are disclosed herein will allow the definition of the function of ABC1, which is critical in deciding the types of modulators are most suitable in therapies.

Any ABC1 function that is detected in the knockout mice of the present invention would provide evidence of the existence of alternative novel ABC1 subtypes which may then be isolated from the knockout mice of the present invention.

The absence of functional ABC1 in the knockout mice of the present invention is confirmed, for example, in RNA analysis, protein expression detection, and other ABC1 functional studies. For RNA analysis, RNA samples are prepared from macrophages harvested from the knockout mice and the ABC1 transcript was detected in Northern blots using DNA probes specific for the transcript.

The ABC superfamily is comprised of myriad transmembrane proteins involved in the transport of vitamins, peptides, ions, sugars and amino acids (Higgins, C. F. ABC-transporters: from microorgansisms to man. *Annu. Rev. Cell Biol.* 8, 67–113 (1992)). A subset of the superfamily contains four closely related proteins (ABC1, ABC2, ABC3 and ABCR) (Luciani, M. F., Denizot, F., Savar, S., Mattei, M. G. & Chimini, G. Cloning of two novel ABC transporters mapping on human chromosome 9. *Genomics* 21, 150–159 (1994). Connors, T. D. et al. The cloning of a human ABC gene (ABC3) mapping to chromosome 16p13.3. *Genomics* 39, 231–234 (1997). Allikmets, R. et al. A photoreceptor cell-specific ATP-binding transporter gene (ABCR) is mutated in recessive Stargardt macular dystrophy. *Nature Genet.* 15, 236–246 (1997)). The protein structure of this subfamily consists of two halves joined by a linker region, each with six transmembrane domains and an ATP-binding cassette site. Several diseases are the result of a dysfunctional ABC transporter—cystic fibrosis, Zellweger syndrome, adrenoleukodystrophy, multidrug resistance and Stargardt macular dystrophy—though the underlying molecular mechanism of the disease is seldom known (Allikmets, R. et al. A photoreceptor cell-specific ATP-binding transporter gene (ABCR) is mutated in recessive Stargardt macular dystrophy. *Nature Genet.* 15, 236–246 (1997). Riordan, J. R. et al. Identification of the cystic-fibrosis gene—cloning and characterization of complementary-DNA. *Science* 245, 1066–1072 (1989). Gartner, J., Moser, H. & Valle, D. Mutations in the 70k peroxisomal membrane-protein gene in Zellweger syndrome. *Nature Genet.* 1, 16–23 (1992). Mosser, J. et al. Putative X-linked adrenoleukodystrophy gene shares unexpected homology with ABC transporters. *Nature* 361, 726–730 (1993). Gottesman, M. M. & Patan, I. Biochemistry of multidrug resistance mediated by the multidrug transporter. *Annu. Rev. Biochem.* 62, 385–428).

The relationship between TD (Tangier disease), FHA (familial hypoalphalipoproteinemia) and mutation in the human ABC1 gene has recently been established by positional cloning of hABC1 from several different families bearing TD or FHA (Bodzioch, M. et al. The gene encoding ATP-binding cassette transporter 1 is mutated in Tangier disease. *Nature Genet.* 22, 347–351 (1999). Brooks-Wilson, A. et al. Mutations in ABC1 in Tangier disease and familial high-density lipoprotein deficiency. *Nature Genet.* 22, 336–345. Rust, S. et al. Tangier disease is caused by mutations in the gene encoding ATP-binding cassette transporter 1. *Nature Genet.* 22, 352–355 (1999)). In each case, point mutations, deletions or frameshifts creates a non-finctional or truncated hABC1 protein. Individuals suffer from reduced or absent HDL-C and lower serum cholesterol and may exhibit discolored tonsils, enlarged spleen and lymph nodes, corneal clouding and neuropathy due to deposition of cholesteryl esters. In other cholesterol metabolic diseases such as Apo A-I deficiency, LCAT deficiency and Fish Eye disease, HDL-C is also reduced but serum cholesterol levels remain normal (Assmann, G., von Eckardstein, A. & Brewer, H. B. Jr Familial high density lipoprotein deficiency: Tangier disease. in *The Metabolic and Molecular Basis of Inherited Disease* (eds Scriver, C. R. et al.) 2053–2072 (McGraw-Hill, New York, 1995)). Low levels of HDL-C usually indicate a high-risk factor for coronary heart disease. Interestingly, the loss of HDL-C in TD patients does not generally cause predisposition to coronary heart disease.

Tangier disease is exceedingly rare, with only 40 reported families worldwide exhibiting the trait. As such, except for the absence of HDL-C, it is difficult to evaluate which symptoms may be directly attributed to a dysfunctional ABC1 transporter. The murine model of Tangier disease, which is described here, confirms the association of ABC1 with TD and exhibits other phenotypes which have not yet been described in humans. The model may further elucidate why the loss of HDL-C does not directly cause coronary heart disease in TD patients.

The human ATP-binding cassette transporter 1 (hABC1), a member of the ABC superfamily, has recently been cloned and analyzed. Frame shift mutations and single base-pair deletions resulting in truncation of hABC1 have been described and linked to familial HDL deficiency (familial hypoalphalipoproteinemia or FHA) and Tangier disease (TD). Both diseases are characterized by the lowering or lack of HDL-C. Low serum cholesterol, splenomegaly, enlarged lymph nodes and the deposition of cholesteryl esters in the reticuloendothelial system are also associated with TD.

The murine ABC1 knockout phenotype corroborates the human TD linkage to ABC1. HDL-C is virtually absent in ABC1 knockout mice accompanied by a reduction in serum cholesterol. In addition to these findings, the placenta of ABC1 knockout mice is often grossly malformed, resulting in severe growth retardation, fetal loss and neonatal death. By six months of age, knockout animals begin to develop membranoproliferative glomerulonephritis due to deposition of immunocomplexes containing both immunoglobulin and complement components. They also develop cardiomegaly with ventricular dilation and hypertrophy and ultimately succumb to congestive heart failure. Tangier disease is exceedingly rare and therefore difficult to study. The creation of a knockout model of TD would be very useful in the study of lipid metabolism and cardiovascular disease. Furthermore, a TD mouse model will clarify the role ABC1 normally plays by permitting exploration of the molecular basis of the disease and revealing previously unsuspected phenotypes.

Human TD has not previously been described as causing developmental problems or defective morphogenesis of the placenta. High level expression of ABC1 mRNA in the placenta, however, has been noted in humans. It is not surprising then, to discover in the murine model of TD that major structural defects exist in the placenta. This supports the purported role of ABC1 in cholesterol trafficking since cholesterol is the starting material for steroid hormones and the placenta is a major site of steroidogenesis. Alterations in cholesterol metabolism due to ABC1 loss may therefore result in the defective formation of the placenta. The inventors contemplate that there may be changes in the level of estrogen, testosterone and progesterone detected during the pregnancy of ABC1 knockout females when compared to pregnant wild-type females. The same alteration in cholesterol metabolism may also result in a reduction in female fertility by altering steroid production during oocyte maturation.

Deposition of cholesteryl esters usually occurs in the reticuloendothelium system in human TD. Previous research with murine macrophages indicates a possible dysfunction in phagocytosis associated with lack of ABC1 function (Luciani, M. F. & Chimini, G. The ATP binding cassette transporter ABC1 is required for the engulfinent of corpses generated by apoptotic cell death. *EMBO J*. 15, 226–235 (1996)). We postulate that ABC1 knockout macrophages may be incapable of phagocytosing immune complexes that form naturally in the blood. Serum sickness or autoimmune disease, both of which cause an immense build-up of immune complexes in the blood, will frequently provoke an inflammatory reaction in the kidney glomeruli, due to immunoglobulin deposition. Failure to phagocytose immune complexes would result in a similar build-up of immune complexes in the blood and deposition of immune complex plaques in the kidney glomeruli. The dilated cardiomyopathy may result from the alterations in kidney function and a failure of the normal renal homeostatic mechanisms that control blood pressure. However, the presence of vasculitis in the vessels of the heart suggests that the loss of ABC1 may lead to a general dysregulation of immune complex formation and/or clearance resulting in a generalized immune complex deposition in multiple organs. The finding that normal macrophage function is affected in both mouse and man with differing outcomes may indicate a relationship between cholesterol metabolism and macrophage phagocytosis.

Loss of ABC1 function results in loss of HDL-C and lowered serum cholesterol. This clearly demonstrates the link between Tangier disease, FHA and dysfunctional ABC1 in humans and establishes that ABC1 plays a role in cholesterol metabolism. Furthermore, the lowered serum cholesterol distinguishes the ABC1 knockout as a model of Tangier disease, distinct from the other cholesterol metabolic diseases. The murine model of Tangier disease further demonstrates that loss of ABC1 function may be more detrimental than previously suspected. The marked female infertility and placental malformation may indicate severe developmental consequences in humans if normal ABC1 function is affected. Finally, the renal failure due to immune complex deposition in knockout animals may indicate a previously unsuspected risk factor among patients with FHA or TD, namely the development of an "autoimmune" mediated disease. Further study of the ABC1 knockout will allow better dissection of lipid metabolism and its connection with early development and the immune system.

The following Examples are presented for the purpose of illustrating the present invention and are not to be construed as a limitation on the scope of this invention.

EXAMPLE 1

Gene Targeting

Mouse ABC1 clones were isolated from a 129/Ola mouse genomic library. The mouse ABC1 gene contains 48 exons (GenBank accession X75926). The knockout construct was composed of 4 parts arranged in a 5' to 3' order, as illustrated in FIG. 1A: (1) A 5 kb DNA fragment from a 129/Ola mouse genomic clone covering exon 18 of the abc1 gene as the long homologous region for recombination. (2) A 1.2 kb DNA cassette containing a neomycin resistant gene with its own promoter and polyadenylation signal that replaced a 1.9 kb DNA region containing exons 19, 20, and part of 21. (3) A 0.8 kb DNA fragment covering part of exon 21 and 22 of the abc1 gene. (4) An HSV-thymidine kinase DNA cassette with its own promoter and polyadenylation signal. The abc1 gene, the neomycin resistant gene and the thymidine kinase gene were in the same orientation of transcription.

In this knockout construct, the mouse abc1 gene was disrupted by deleting exons 19, 20 and a portion of exon 21, which encode most of the first ATP binding cassette of the ABC1 protein.

Transfection of ES Cells with the abc1 DNA Construct

Embryonic stem (ES) cells E14 (Hooper et al., 1987, HPRT-deficient (Lesch-Nyhan) mouse embryos derived from germline colonization by cultured cells,) Nature 326, 292–295) were maintained at an undifferentiated stage by co-culturing with embryonic fibroblasts (EF) and in culture medium DMEM (15% FCS, 1 mM sodium pyruvate, 0.1 mM b-mercaptoethanol, 2 mM L-glutamine, 100 U penicillin and 100 U streptomycin) containing 1000 U/ml leukemia inhibitory factor (LIF) (Gibco). EF cells were primary fibroblast cultures prepared from day 15–17 mouse fetuses according to the method described by Robertson (Robertson, E. J. (1987) Embryo-derived Stem Cell Lines. In: Teratocarcinomas and Embryonic Stem Cells. E. J. Robertson, ed. (Oxford, Washington DC: IRL Press), p 71–112.). EF cells were treated with 10 mg/ml mitomycin C (Sigma) in culture medium for 2 hours to stop cell division prior to their use as feeder cells.

For DNA transfection, the DNA construct was linearized by NotI digestion. DNA was then precipitated by 2 volumes of ice cold ethanol at −20° C. for 1 hour. Precipitated DNA was pelleted by centrifugation, rinsed once with 0.5 ml 70% ethanol, air dried and then dissolved at 1 mg/ml in phosphate-buffered saline (Gibco). ES cells were harvested by trypsin treatment and resuspended at $6.25 \times 10^6$ cell/ml in culture medium. DNA construct (20 μg) was added to 0.8 ml of ES cell suspension for electroporation at 250 μF and 340 Volts using the Gene Pulser (BioRad).

Transfected ES cells were plated onto EF coated 90 mm plates at $2.5 \times 10^6$/plate in culture medium. Two days later, cells were subjected to drug selection in medium containing 400 μg/ml G418 (Geneticin, Gibco) and 0.2 μM ganciclovir. Culture medium was changed daily. Massive cell death was obvious starting day 4 and most of the dead cells were removed through daily medium change. Surviving cell colonies were observable under microscope by day 7 and by day 10 they were visible on the plates without a microscope.

PCR screen of Transfected ES Cells for Homologous Recombination

The size of ES colonies on day 11 after transfection was large enough for PCR screening. To collect cell colonies, culture medium in the 90 mm plates was aspirated and 10 ml PBS was added. Individual cell colonies were located with the aid of a stereomicroscope, collected in a 20 ml volume with an autopipetteman and transferred into 96 well-plates. To prepare single cell suspension of the ES colonies, 25 μl of 0.25% trypsin (Gibco) was added per well in 96 well-plates. After 8 minutes of trypsin treatment at 37° C., 25 μl of culture medium was added. All the ES colonies were still maintained in culture as master plates while screening by PCR for homologous recombination events was performed. To prepare master plates, 60 μl of each cell sample was transferred to 96-well plates which had been coated with EF cells and contained 180 μl/well of the culture medium containing G418 and ganciclovir.

For the first round PCR screen, each cell lysate sample was prepared from 12 cell colonies which arrayed as one row of samples in the 96 well-plates. After the preparation of master plates, the remaining cell samples of about 90 μl/well on every row of the plates were pooled. Cells were pelleted in tubes by centrifugation for 1 minute. After draining all the medium, cells were lysed by adding 30 μl distilled water and brief vortexing. Cell lysates were prepared by first heating at 95° C. for 10 minutes, cooling to room temperature and followed by an addition of 1 μl proteinase K (10 mg/ml in water) with brief vortexing, a 90 minute incubation at 50° C. for proteinase K digestion, and then 10 minutes at 95° C. for heat inactivation of proteinase K.

PCR was carried out using the 9600 GeneAmp system (Perkin Elmer). The reaction mixtures contained 5 μl cell lysate, 4 μM of each of the two oligonucleotide primers, 200 μM each of dATP, dTTP, dCTP, and dGTP, and 5 U Ampli-Taq DNA polymerase in PCR buffer (10 mM Tris-Cl, pH8.3, 50 mM KCl, 1.5 mM MgCL$_2$ and 0.001% w/v gelatin). The 5' primers ABC3057 [SEQ.ID.NO.:1] 5'-GAGCACATCTGGTTCTATGC-3' and Neo1455 [SEQ.ID.NO.:2] 5'-GCTTCCTCGTGCTTTACGGTAT-3' were specific for the endogenous and altered ABC1 gene, respectively. The 3' primer ABC210R [SEQ.ID.NO.:3] 5'-AAGACACGGTGCTGCTACTGTT-3' was specific for the abc1 gene in a region flanking the 3' end of the knockout construct. The wild-type abc1 gene was detected by primers ABC3057 and ABC210R in PCR amplification as a DNA band of 1.3 kb. The disrupted abc1 gene was amplified by primers Neo1455 and ABC210R as a DNA band of 1.0 kb. The PCR reaction was 2 cycles of 1 minute at 94° C., 1 minute at 54° C., 2 minutes at 72° C., for 2 cycles; then 40 cycles of 15 at 94° C., forty seconds at 54° C., one minute and thirty seconds at 72° C., and finally a 5 minute elongation period at 72° C.

ES cells in master plates after 3–4 days culture were ready for splitting. Cell colonies in the positive groups were screened individually by a second round of PCR to identify the positive individual colonies. To maintain the positive groups in culture, cells in the wells were trypsinized by first removing the culture medium, rinsing once with 50 μl PBS, treating with 40 μl 0.25% trypsin for 5 minutes at 37° C., followed by adding 90 μl culture medium. Cells were then resuspended and 20 μl of the cell samples were transferred to master plates which had been coated with EF and filled with 200 μl culture medium containing G418 and ganciclovir. The remaining cells (110 μl/well) were transferred into eppendorf tubes. Cell lysates were prepared and homologous recombination signals were amplified by PCR and detected by hybridization as described in the previous paragraphs.

Confirmation of Homologous Recombination by Genomic Southern Hybridization

Homologous recombination was confirmed by Southern hybridization. ES cells derived from the positive colonies in PCR screen were expanded in culture and DNA was extracted as described by Maniatis et al. (Maniatis, T.; Fritsch, E. F.; Sambrook, J. (1982) Molecular Cloning, Cold Spring Harbor Laboratory pp. 280–281). Genomic DNA samples of the putative knockout cell lines were digested with the restriction enzymes EcoRI, separated by 1% agarose gel electrophoresis, blotted onto Hybond-N+ nylon membranes (Amersham) and hybridized with a 253 bp DNA probe specific for the mouse abc1 gene that was 3' to the knockout region. This DNA probe fragment was obtained by PCR using the abc1 gene-specific oligonucleotides ABC547 [SEQ.ID.NO.4:] (5'-CCTACCTGCTGCCTTAAATCT-3') and ABC800R [SEQ.ID.NO.5:] (5'-ATGCTACAGTTCCTACAAGC-3'). This probe hybridizes to a 2.2 kb band from EcoRI digested ABC1 gene and to a 2.6 kb band from a knockout ABC1 gene. As seen in FIG. 1C, the wild-type animals demonstrate a single 2.2 kb band, while heterozygotic animals demonstrate two bands, 2.2 kb and 2.6 kb. This DNA probe did not hybridize to the DNA constructs that were integrated randomly in the chromosome.

Generation of Chimeric Mice by Embryo Injection

Mouse embryos at 3.5 day gestation stage were collected from the uteri of super-ovulated C57BL/6J mice. About 10–15 ES cells were injected into the blastocoel cavity of the embryos. Injected embryos were transferred into the uteri of pseudo-pregnant CD1 mice at 2.5 day gestation. Mice developed from these embryos were born 17 days later. Since the ES cells used were derived from the 129 Ola mouse strain with the dominant agouti coat color genes, chimeric mice were identified by the agouti coat color from ES derived cells, versus the black color from C57BL/6J mouse embryos.

ES Germline Mice obtained by Chimeric Mouse Breeding

Chimeric mice were bred with C57BL/6J mice. These crosses are performed to test for the germline transmission of ES cells. Some of the progeny from the breeding are expected to be agouti if the chimeric male had germ line cells derived from ES cells which carry the dominant agouti coat color genes. The disrupted abc1 gene in mice was detected by genomic hybridization as described in the previous section. Genomic DNA is purified from about 1 cm of tail from each agouti mouse after weaning. The genomic DNA is isolated as described (Laird et al., supra), followed by phenol and phenol:chloroform extractions and ethanol precipitation. Genomic DNAs are digested with EcoRI, and hybridized with the 3' flanking DNA specific for the abc1 gene as described earlier.

Generation of Homozygous Knockout Mice from Breeding of Heterozygous Knockout Mice Female heterozygous knockout mice were mated with male heterozygous knockout littermates. It is expected that half of the pups are heterozygous for the disrupted gene, one-quarter carry only the disrupted gene and one quarter carry only the wild-type gene. Surviving offspring were genotyped by Southern hybridization as described above. Continued breeding of homozygous knockout mice were maintained by crossing heterozygous females with knockout males. As shown in FIG. 1B, mice that were wild-type, heterozygous and homozygous for the disrupted abc1 gene were identified by the PCR method described in the previous paragraph.

EXAMPLE 2

Characterization of ABC1 Knockout Mice and Cells Derived From the Mice Lipid Analysis Cholesterol and HDL-C from six mice of each genotype were analyzed by standard enzymatic means on an Olympus AU520 mulitchannel analyser (Quest Diagnostics, San Diego, Calif.).

HDL Loss is the Direct Result of ABC1 Dysfunction.

The primary hallmark of Tangier disease is the lack of HDL-C and lowered serum cholesterol, often accompanied by neuropathy, discoloration of the tonsils, clouding of the cornea and enlargement of the spleen and lymph nodes due to deposition of cholesteryl esters (Assmann, G., von Eckardstein, A. & Brewer, H. B. Jr Familial high density lipoprotein deficiency: Tangier disease. in *The Metabolic and Molecular Basis of Inherited Disease* (eds Scriver, C. R. et al.) 2053–2072 (McGraw-Hill, New York, 1995)). Assessment of the physiological consequences of a non-functioning ABC1 transporter is difficult due to the limited number of TD cases. FHA is a more common disease, but apparently is caused by multiple factors. Functional loss of ABC1 in a murine model clearly demonstrates that the major characteristic of TD, lack of HDL-C, is present and substantiates the link between mutated ABC1 and TD. Like TD patients, HDL-C levels in ABC1 knockout mice are almost non-existent while in heterozygous mice HDL-C levels are roughly one-half of the levels found in normal mice. Cholesterol levels are also significantly reduced in a similar manner (Table I).

TABLE I

HDL-C and Cholesterol Levels in ABC1 Knockout Mice are Significantly Reduced

| Genotype | HDL-C (mg/dL) | Cholesterol (mg/dL) |
|---|---|---|
| Wild-Type | 77.3 ± 6.1 | 100.7 ± 6.2 |
| Heterozygous | 41.0 ± 8.9 | 60.2 ± 13 |
| Homozygous | 2.3 ± 0.5 | 22.6 ± 9.8 |

Few of the other symptoms associated with TD in human patients have been noted in ABC1 knockout mice. Splenomegaly and minor swelling of the lymph nodes with finely lined yellow-white traceries radiating outwards has occasionally been noted. Taken together, this data indicates that the murine version of Tangier disease is identical to the human disease with regard to HDL-C loss and lowering of serum cholesterol.

In-situ Hybridization

Tissue sections were mounted onto poly-L-lysine coated slides and fixed an additional 30 min in 10% formalin, digested with proteinase K (10 $\mu$g/ml in 50 mM Tris HCl, pH 7.5, and 5 mM EDTA) for 30 min, at 37° C., followed by acetylation (0.25% acetic anhydride in 0.1M triethanolamine, pH 8.0) and dehydration by alcohol. Each slide received 100 $\mu$l of hybridization mixture, containing the $^{35}$S-UTP labeled probe LM243 ($10^7$ cpm/ml). The slides were coverslipped and incubated at 60° C. in an oven overnight.

After the incorporation of labeled probe overnight, the tissue was treated with 20 $\mu$g/ml of ribonuclease A for 30 min, at 37° C., washed for 30 min in 15 mM NaCl/1.5 mM sodium citrate (SSC) at 70° C., dehydrated with ethanol and exposed to X-ray films for 6 days. The slides were then defatted in xylene, rinsed in ethanol, dried, dipped in NBT2 nuclear emulsion (Eastman Kodak, Rochester, N.Y., diluted 1:1 with distilled water), and stored in the dark at 4° C. Following 22 days, slides were developed in D-19 (Eastman Kodak) for 3.5 min at 14° C., rinsed in distilled water, fixed with Polymax T Fixer (Eastman Kodak) for 4 min at 14° C., and washed in distilled water for 1 h. We defined positively labeled cells as any accumulation of silver grains within a cell-sized area that was five times above background or control levels. Antisense and sense (control) cRNA probes for the ABC1 were generated from the cDNAs. Labeled antisense and sense probes for the ligand were synthesized following linearization with HindIII or EcoRI, using T3 or T7, respectively. The cDNA was purified with Qiagen (Santa Clarita, Calif.) following the linearization. Probes were labeled with $^{35}$S-UTP. Unincorporated nucleotides were removed by G-50 Sephadex Quick Spin columns (Boehringer Mannheim, Mannheim, Germany). The labeled sense strands served as controls and did not show any specific labeling of cellular localization. All restriction enzymes and RNA polymerases were obtained from Boehringer Mannheim. Reference for In-Situ: Simmons, D. M., Arriza, J. L. & Swanson, L. W. A complete protocol for in situ hybridization of messenger RNAs in brain and other tissues with radiolabeled single-stranded RNA probes. *J. Histotechnol.* 12, 169–181(1989).

Loss of ABC1 Results in Severe Placental Malformation and Oxidative Distress.

Figure 2:
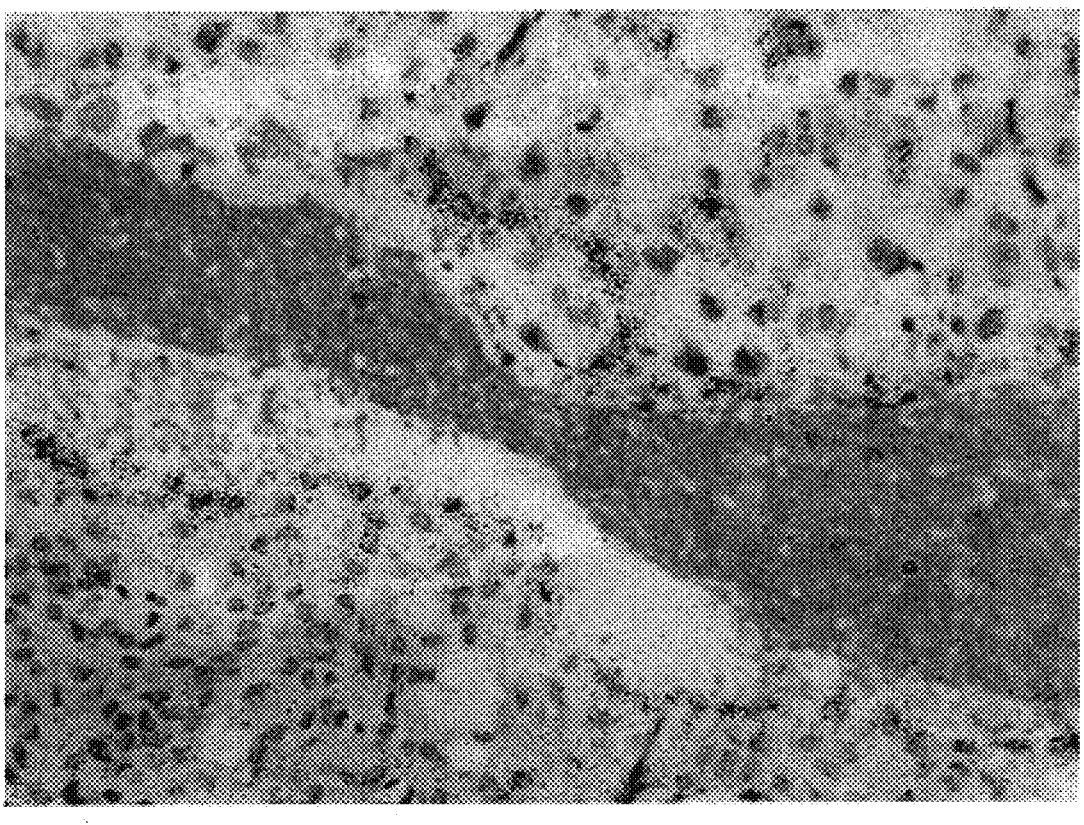
FIG. 2. In-situ hybridization of ABC1 mRNA lining maternal decidual blood vessel derived from placenta, magnification 250×.
Figure 3A:
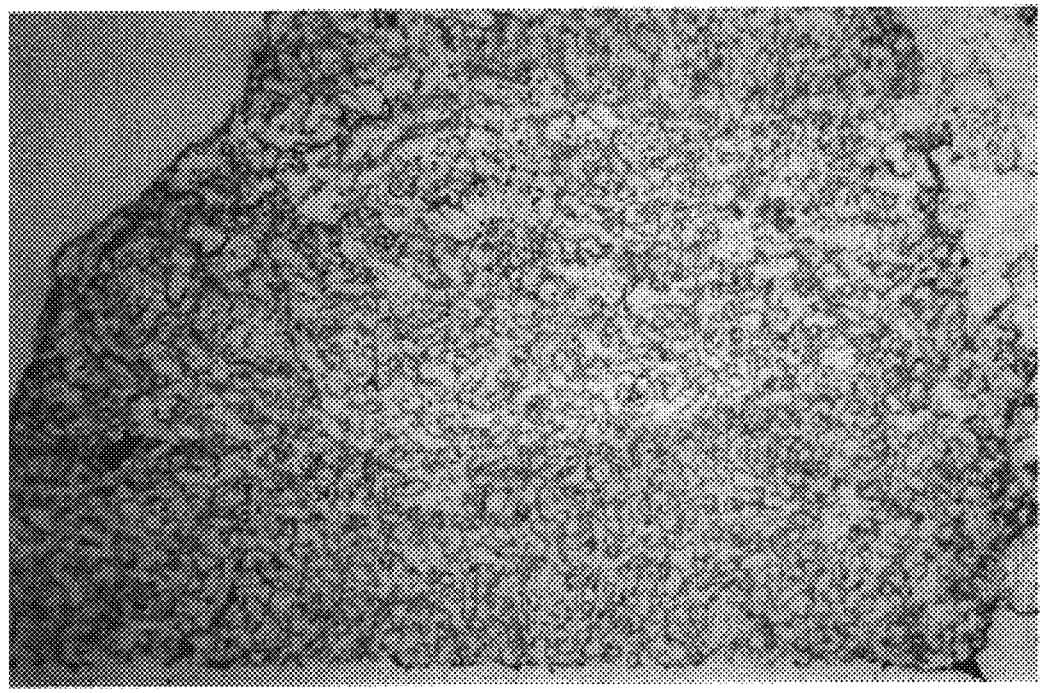
FIGS. 3A–E: Placenta malformation and oxidative distress in ABC1 knockout mice. [Panel 1] A) Day 14 placenta labyrinth from ABC1 knockout mouse line 64.7 stained with CD71, knockout (top) and wild-type (bottom), magnification 100×. [Panel 2] B) H&E stained day 14 placenta labyrinth knockout (top) and wild-type (bottom), magnification 63×. [Panel 3] C) Day 14 p.c. ABC1 knockout embryos demonstrating gradation of intrauterine growth retardation. [Panel 4] D) Day 19 embryos with amniotic sac, knockout (top) and wild-type (bottom). [Panel 5] E) H&E stained lungs from one-day-old neonates, knockout (top) and wild-type (bottom), magnification 100×.
Figure 3A:
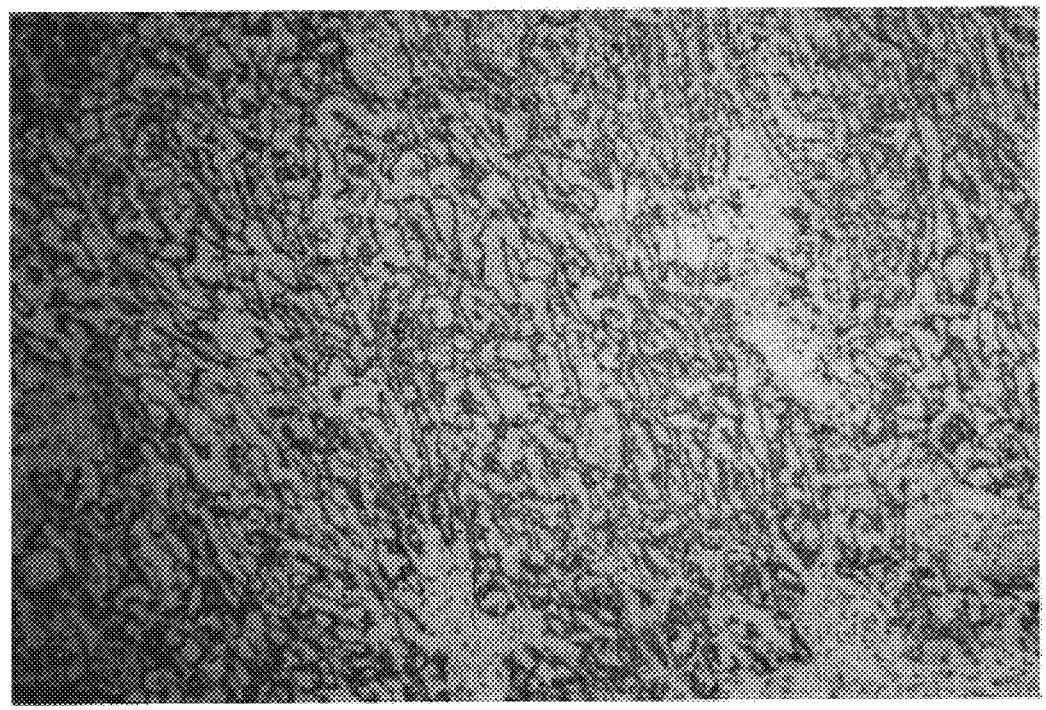
Figure 3B:
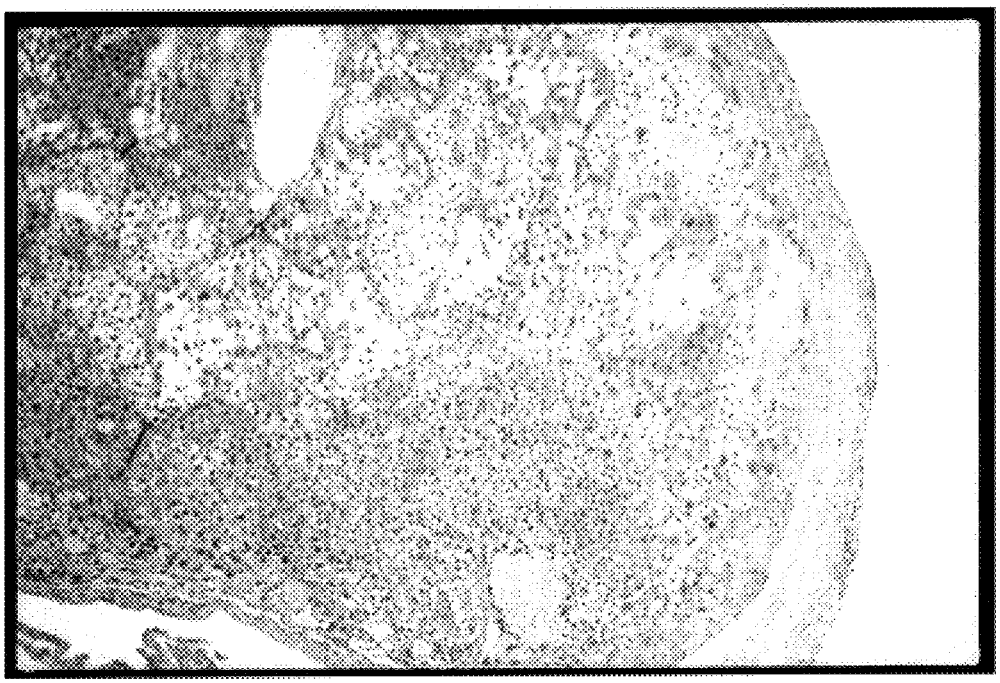
Figure 3B:
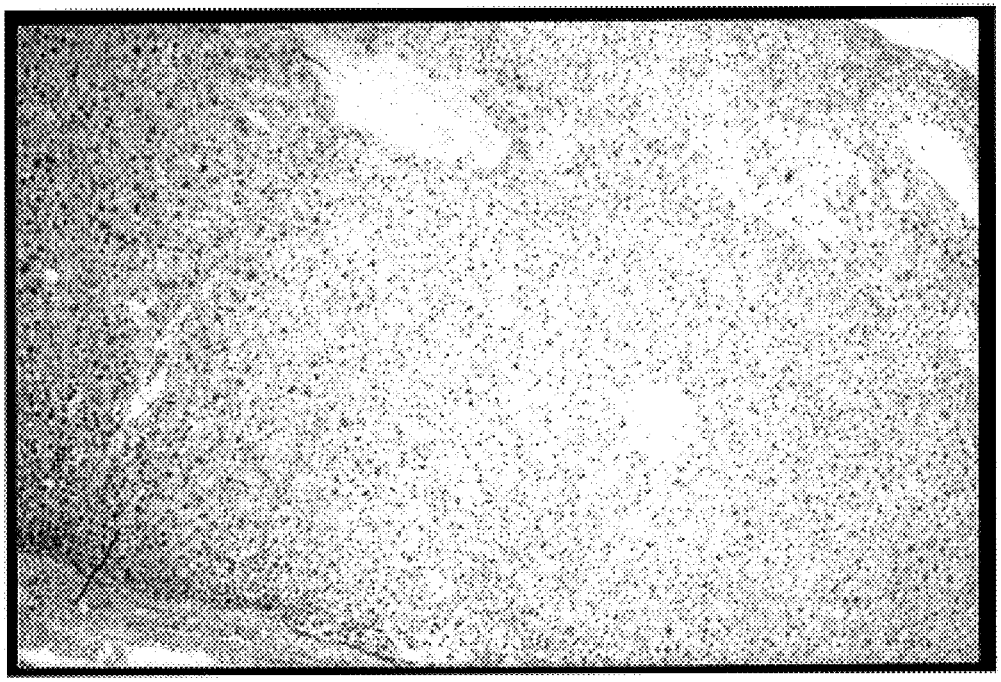
Figure 3C:
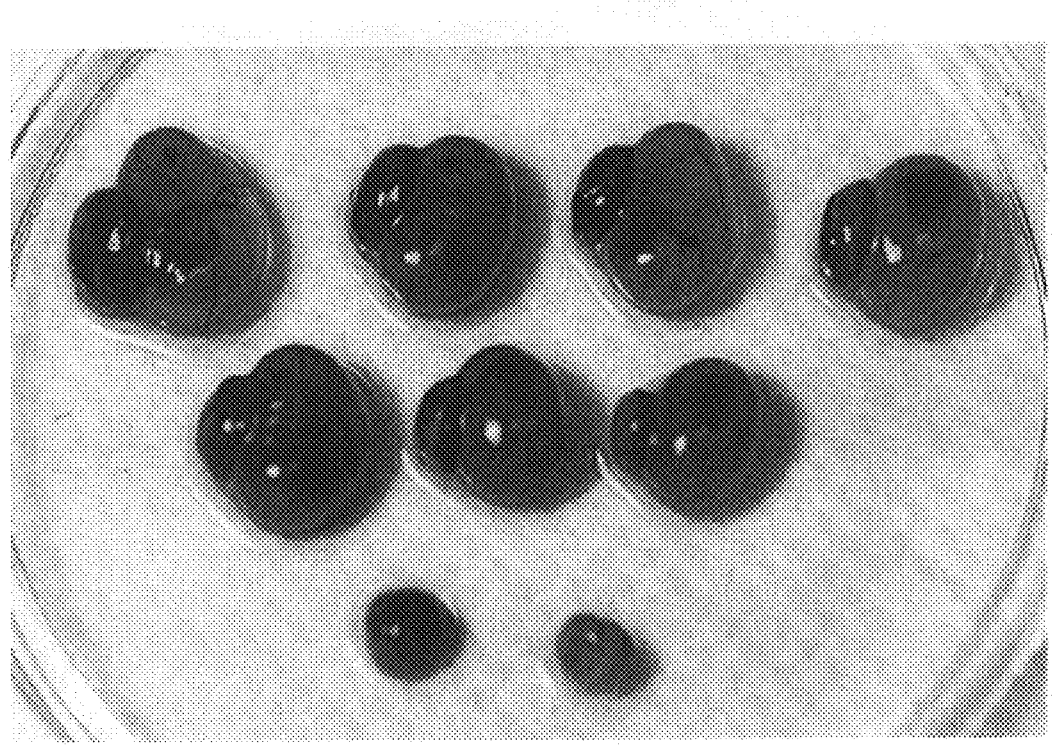
Figure 3D:
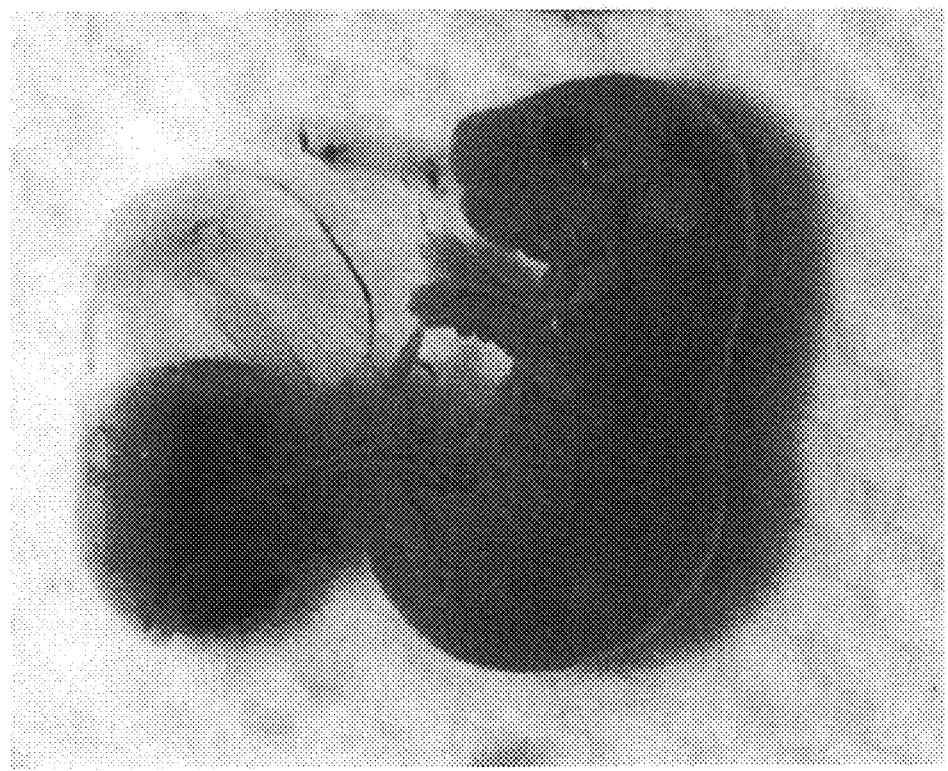
Figure 3E:
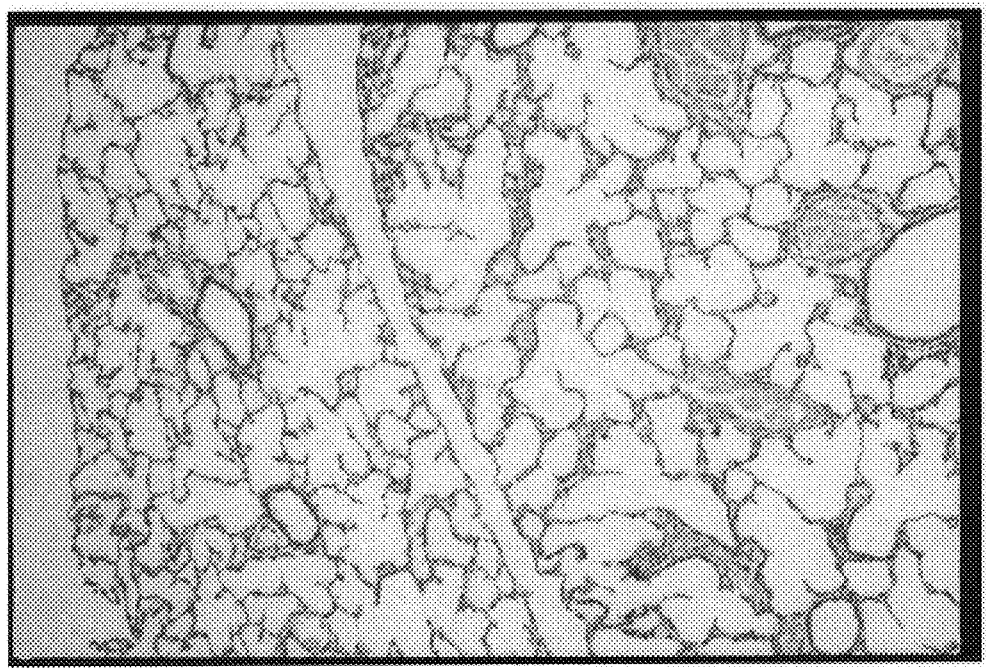

Other phenotypic traits that could be characteristic of TD may escape detection because the disease is so rare, especially if they are fatal at an extremely early stage of development. The highest level of ABC1 mRNA expression in humans is in the placenta (Luciani, M. F. & Chimini, G. The ATP binding cassette transporter ABC1 is required for the engulfment of corpses generated by apoptotic cell death. *EMBO J.* 15, 226–235 (1996)). In mice, ABC1 mRNA expression is clearly seen lining a decidual maternal blood vessel of the placenta and is present throughout the trophoblast (FIG. 2). Placenta derived from an ABC1 knockout fetus from either the 55.2 or 64.7 lines shows various degrees of defects ranging from an almost normal structure to a badly distorted, functionally impaired tissue. Placenta from ABC1 heterozygote fetus also appears slightly abnormal. The structure of the labyrinthine trophoblasts is the most malformed. A well-formed labyrinth is comprised of a lacy, open structure with a consistent symmetry. In most knockout placenta the labyrinth is much more cellular and the symmetry is distorted (FIG. 3A). Hemorrhages, cell debris and ragged inclusions of the spongiotrophoblast are prevalent (FIG. 3B). These defects may compromise oxygen exchange between mother and fetus. In homozygous crosses, intrauterine growth retardation is evident, accompanied by fetal death and resorption in utero as early as day 14 p.c. (FIG. 3C). As pregnancy progresses, fetal distress becomes even more apparent. At day 19 p.c. the amniotic sacs are stained brown, consistent with the release of meconium into the amniotic fluid (FIG. 3D). Often half of the remaining pups are dead in utero, as measured by lack of reflexive movement. Pups that survive to be born often succumb in the first 24–48 hours after birth. Autopsy indicates the lungs are congested with blood and are extremely cellular (FIG. 3E). The histology is reminiscent of bronchopulmonary dysplasia, the sequelae of hyaline membrane disease. It may also indicate inhalation of meconium-tainted amniotic fluid in utero. Finally, a handful of neonates runt as early as five days after birth and die from similar causes by 2.5 weeks. Heterozygous crosses of ABC1 mice results only an 8% survival rate of knockouts (176 animals analyzed—Table II). This survival rate is increased to 28% in heterozygote/homozygote crosses (76 animals analyzed). Interestingly, a marked sex bias against male homozygotes is present. Only one-quarter of the male homozygotes survive (6.5%) compared to the expected Mendelian ration for male homozygotes (25%). Lastly, only 10% of female homozygotes ever succeed in bearing 1–2 viable offspring. Thus, loss of functional ABC1 consequently results in a severe developmental defect of the placenta, leading to intrauterine growth retardation and neonatal death and markedly reduces female fertility.

TABLE II

Mendelian Ratios of ABC1 Mating are Biased Against Knockout Mice

| Cross (male × female) | Genotype | | |
| --- | --- | --- | --- |
|  | Wild-Type | Heterozygote | Homozygote |
| Heterozygote × Heterozygote | 34% | 56% | 8% |
| Homozygote × Heterozygote | — | 72% | 28% |

Loss of ABC1 Results in Immune Complex Deposition in Kidney Glomeruli and Congestive Heart Failure.

Figure 4A:
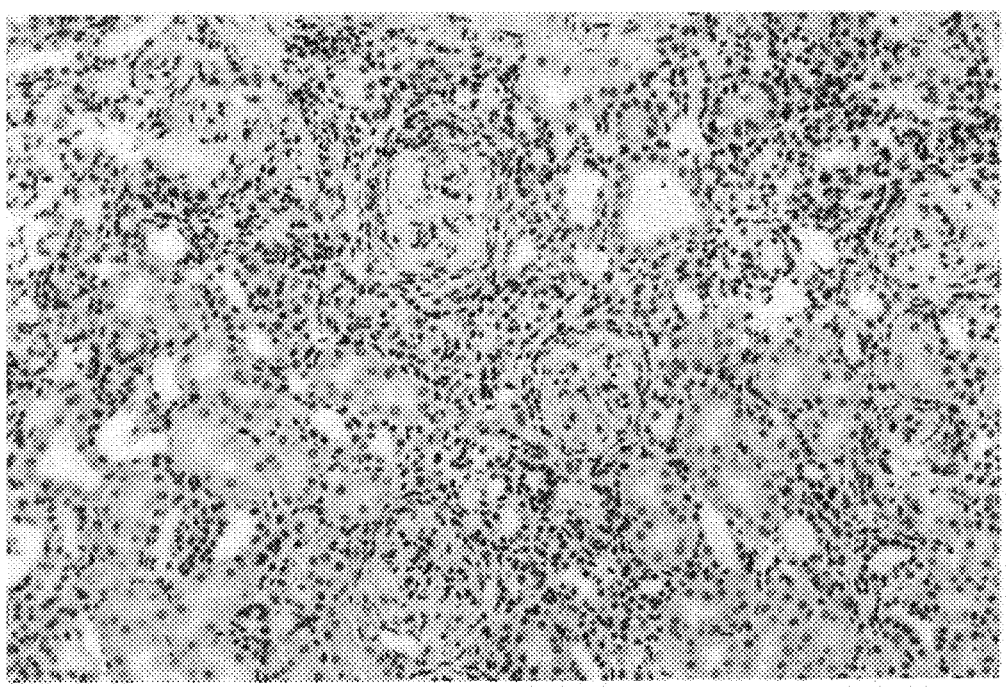
FIGS. 4A–B: Kidney glomeruli nephritis and immunoglobulin deposition. [Panel 1] A) H&E stained kidney sections from diseased ABC1 knockout mouse line 55.2 (top) and healthy wild-type (bottom). [Panel 2] B) Heavy deposition of immunoglobulin in glomeruli of ABC1 knockout mouse line 64.7 (top) and Normal glomeruli (bottom).
Figure 4A:
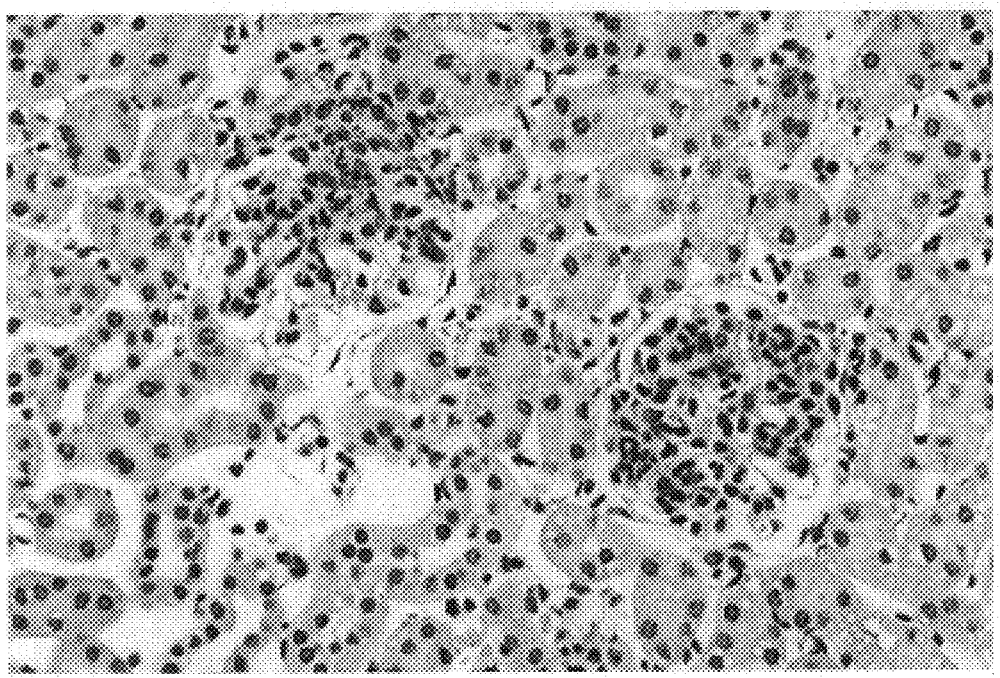
Figure 4B:
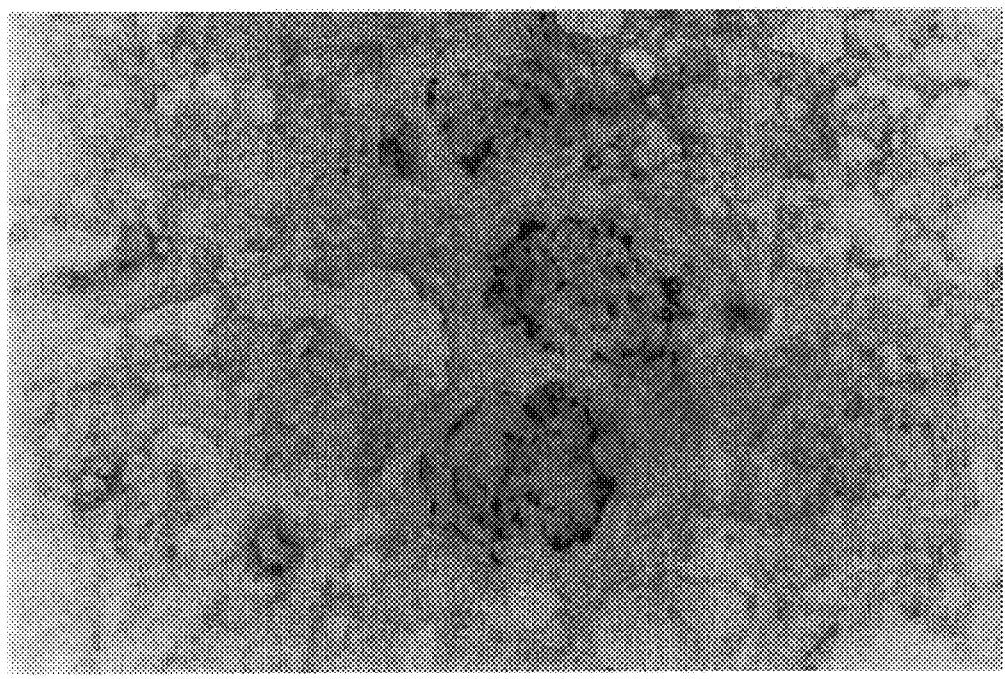
Figure 4B:
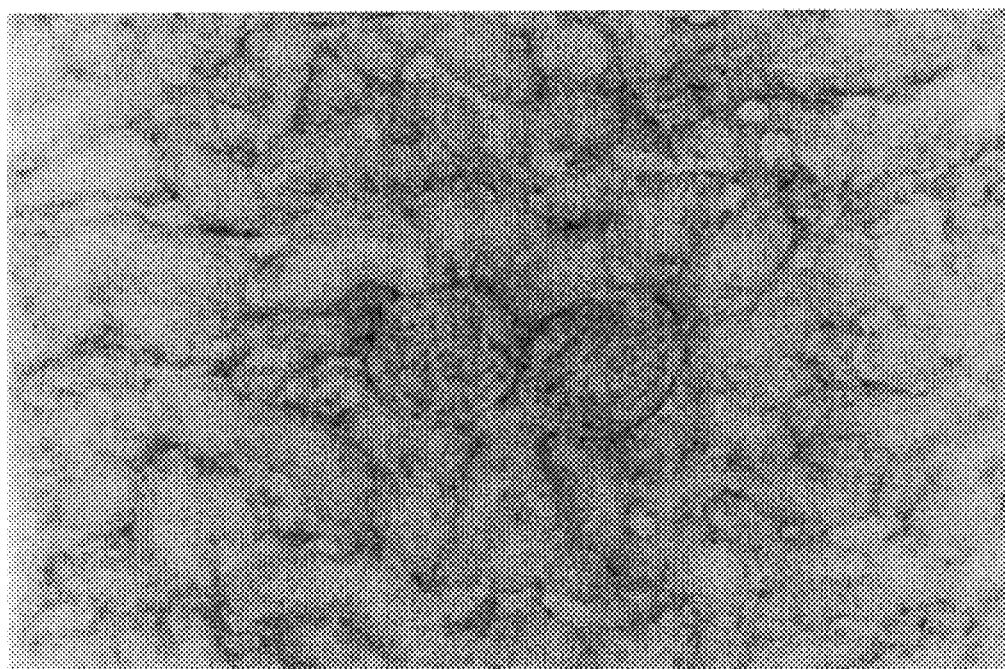

ABC1 knockout mice that survive to be weaned appear to develop normally and mature into apparently healthy adults. Between 4–6 months of age the mice of both lines begin to develop respiratory distress and shed granular casts into their urine. Necropsy examination reveals lungs heavily filled with blood and cardiomegaly with dilated hypertrophied left and right ventricles. There is occasional evidence of vasculitis around the cardiac vessels. The kidneys are pale tan in color. Microscopic examination reveals boxcar nuclei in the heart consistent with cardiac hypertrophy with frank pulmonary hemorrhages as well as severe congestion of the lungs, liver and spleen, and scarred kidney glomeruli. The glomeruli show evidence of inflammatory infiltrates, thickened and "split" glomerular basement membranes and proliferation of mesangial cells. Scarring of glomeruli was visible when sections were stained with trichrome (FIG. 4A). Immunohistochemistry confirms the deposition of both Ig and C3 complement components in the glomeruli characteristic of membranoproliferative glomerulonephritis type I (FIG. 4B). To summarize, in knockout ABC1 mice we find evidence of immune complex and complement deposition in kidney glomeruli, inflammation, glomeruli nephritis, cardiomegaly and congestive heart failure.

References:

1. Higgins, C. F. ABC-transporters: from microorganisms to man. *Annu. Rev. Cell Biol.* 8, 67–113 (1992).
2. Luciani, M. F., Denizot, F., Savar, S., Mattei, M. G. & Chimini, G. Cloning of two novel ABC transporters mapping on human chromosome 9. *Genomics* 21, 150–159 (1994).
3. Connors, T. D. et al. The cloning of a human ABC gene (ABC3) mapping to chromosome 16p13.3. *Genomics* 39, 231–234 (1997).
4. Allikmets, R. et al. A photoreceptor cell-specific ATP-binding transporter gene (ABCR) is mutated in recessive Stargardt macular dystrophy. *Nature Genet.* 15, 236–246 (1997).
5. Riordan, J. R. et al. Identification of the cystic-fibrosis gene—cloning and characterization of complementary-DNA. *Science* 245, 1066–1072 (1989).
6. Gartner, J., Moser, H. & Valle, D. Mutations in the 70k peroxisomal membrane-protein gene in Zellweger syndrome. *Nature Genet.* 1, 16–23 (1992).
7. Mosser, J. et al. Putative X-linked adrenoleukodystrophy gene shares unexpected homology with ABC transporters. *Nature* 361, 726–730 (1993).
8. Gottesman, M. M. & Patan, I. Biochemistry of multi-drug resistance mediated by the multidrug transporter. *Annu. Rev. Biochem.* 62, 385–428.
9. Bodzioch, M. et al. The gene encoding ATP-binding cassette transporter 1 is mutated in Tangier disease. *Nature Genet.* 22, 347–351 (1999).
10. Brooks-Wilson, A. et al. Mutations in ABC1 in Tangier disease and familial high-density lipoprotein deficiency. *Nature Genet.* 22, 336–345.
11. Rust, S. et al. Tangier disease is caused by mutations in the gene encoding ATP-binding cassette transporter 1. *Nature Genet.* 22, 352–355 (1999).
12. Assmann, G., von Eckardstein, A.. & Brewer, H. B. Jr Familial high density lipoprotein deficiency: Tangier disease. in *The Metabolic and Molecular Basis of Inherited Disease* (eds Scriver, C. R. et al.) 2053–2072 (McGraw-Hill, New York, 1995).
13. Langmann, T. et al. Molecular cloning of the human ATP-binding cassette transporter 1 (hABC1): evidence for sterol-dependent regulation in macrophages. *Biochem. Biophys. Res. Commun.* 257, 29–33 (1999).
14. Luciani, M.F. & Chimini, G. The ATP binding cassette transporter ABC1 is required for the engulfinent of corpses generated by apoptotic cell death. *EMBO J.* 15, 226–235 (1996).
15. Simmons, D. M., Arriza, J. L. & Swanson, L. W. A complete protocol for in situ hybridization of messenger RNAs in brain and other tissues with radiolabeled single-stranded RNA probes. *J. Histotechnol.* 12, 169–181(1989).

What is claimed is:

1. A transgenic mouse whose somatic and germ cells comprise a disruption in an endogenous abc1 gene, wherein said disruption is generated by targeted replacement with a non-functional abc1 gene, and wherein said disruption results in said mouse having a decrease in the amount of serum cholesterol compared to a wild-type abc1 mouse.

2. The mouse of claim 1, wherein said mouse is fertile and transmits the non-functional abc1 gene to its offspring.

3. The mouse of claim 1, wherein the non-functional abc1 gene has been introduced into an ancestor of the mouse at an embryonic stage by microinjection of embryonic stem cells into mouse blastocysts.

4. The mouse of claim 1, wherein the non-functional abc1 gene has been introduced at an embryonic stage by microinjection of embryonic stem cells into mouse blastocysts, wherein said mouse blastocysts are introduced into a pseudopregnant mouse which gives rise to said transgenic mouse.

5. A method for producing a transgenic mouse whose somatic and germ cells comprise a disruption in an endogenous abc1 gene, wherein said disruption is generated by targeted replacement with a non-functional abc1 gene, said method comprising:

(a) introducing an abc1 gene targeting construct comprising a selectable marker sequence into a mouse embryonic stem cell;

(b) introducing said mouse embryonic stem cell into a mouse blastocyst;

(c) transplanting said blastocyst into a recipient pseudopregnant mouse;

(d) allowing said blastocyst to develop to term;

(e) identifying a transgenic mouse whose genome comprises a disruption of an endogenous abc1 gene in at least one allele; and (f) breeding the mouse of step (e) to obtain a transgenic mouse whose genome comprises a homozygous disruption of the endogenous abc1 gene, wherein said disruption results in said mouse having a decrease in the amount of serum cholesterol as compared to wild-type abc1 mice.

6. The method of claim 5 wherein the introducing of step (a) is by electroporation or microinjection.

* * * * *